(12) United States Patent
Wittkampf et al.

(10) Patent No.: US 8,454,538 B2
(45) Date of Patent: Jun. 4, 2013

(54) FILTERING METHOD FOR SURFACE MODELING

(75) Inventors: Frederik H. Wittkampf, Bilthoven (NL); John Hauck, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 13/015,643

(22) Filed: Jan. 28, 2011

(65) Prior Publication Data

US 2011/0125008 A1    May 26, 2011

Related U.S. Application Data

(63) Continuation of application No. 11/647,591, filed on Dec. 29, 2006, now Pat. No. 7,894,871.

(51) Int. Cl.
*A61B 5/103* (2006.01)
(52) U.S. Cl.
USPC .......................................... 600/587; 600/549
(58) Field of Classification Search
USPC ........................................................ 600/549
See application file for complete search history.

(56) References Cited

U.S. PATENT DOCUMENTS

| | | | |
|---|---|---|---|
| 3,250,012 A | 5/1966 | Hilton et al. | |
| 5,297,549 A | 3/1994 | Beatty et al. | |
| 5,311,866 A | 5/1994 | Kagan et al. | |
| 5,480,422 A | 1/1996 | Ben-Haim | |
| 5,492,131 A | 2/1996 | Galel | |
| 5,568,809 A | 10/1996 | Ben-haim | |
| 5,662,108 A | 9/1997 | Budd et al. | |
| 5,718,241 A | 2/1998 | Ben-Haim et al. | |
| 6,083,170 A * | 7/2000 | Ben-Haim | 600/463 |
| 6,226,542 B1 | 5/2001 | Reisfeld | |
| 6,371,930 B1 | 4/2002 | Shafir | |
| 6,858,003 B2 | 2/2005 | Evans et al. | |
| 2002/0055674 A1 | 5/2002 | Ben-Haim et al. | |
| 2002/0077568 A1* | 6/2002 | Haddock | 600/587 |
| 2002/0087089 A1 | 7/2002 | Ben-Haim | |
| 2002/0096642 A1 | 7/2002 | Massie | |
| 2004/0254437 A1 | 12/2004 | Hauck et al. | |
| 2005/0137478 A1 | 6/2005 | Younge et al. | |

(Continued)

FOREIGN PATENT DOCUMENTS

| | | |
|---|---|---|
| EP | 1070480 | 1/2001 |
| EP | 1125549 | 8/2001 |

(Continued)

OTHER PUBLICATIONS

Takashima et al. "Contact and friction between catheter and blood vessel" 2006, as submitted by applicant.*

(Continued)

*Primary Examiner* — Max Hindenburg
*Assistant Examiner* — Renee Danega
(74) *Attorney, Agent, or Firm* — Wiley Rein LLP

(57) ABSTRACT

A system for mapping a tissue surface includes a probe for mapping a tissue surface, a localization system to measure a location data point indicative of the probe's location, a memory in which to store the location data point, a servo mechanism to move the probe along at least a portion of the tissue surface, a controller to move the probe to a plurality of locations and to record in the memory a plurality of location data points, and a contact-sensing processor to analyze the plurality of location data points and to identify a subset thereof on the tissue surface. A modeling processor generates a model of the tissue surface using the subset of location data points. The contact-sensing processor utilizes probe velocity, or a rate of change in the distance moved by the probe, to determine contact between the probe and the tissue surface.

12 Claims, 5 Drawing Sheets

U.S. PATENT DOCUMENTS

| | | | |
|---|---|---|---|
| 2005/0240116 A1* | 10/2005 | Saadat et al. | 600/549 |
| 2006/0009735 A1 | 1/2006 | Viswanathan et al. | |
| 2006/0276775 A1 | 12/2006 | Rosenberg et al. | |

FOREIGN PATENT DOCUMENTS

| | | |
|---|---|---|
| WO | 97/24981 | 7/1997 |
| WO | 01/08555 | 2/2001 |
| WO | 2006/121883 | 11/2006 |

OTHER PUBLICATIONS

Takashima et al., "Contact and friction between catheter and blood vessel," Tribology International 2007; 40; 319-328 (Mar. 29, 2006).
International Search Report and Written Opinion of PCT/US0788671 dated Jun. 26, 2008.

* cited by examiner

FILTERING METHOD FOR SURFACE MODELING

CROSS-REFERENCE TO RELATED APPLICATIONS

This application is a continuation of U.S. application Ser. No. 11/647,591, filed 29 Dec. 2006, now allowed, which is hereby incorporated by reference as though fully set forth herein.

BACKGROUND OF THE INVENTION a. Field of the Invention

The instant invention relates to modeling of tissue surfaces. In particular, the instant invention relates to a system and method for distinguishing surface points from interior points during the collection of geometry points.

b. Background Art

It is well known to generate heart chamber geometry in preparation for cardiac diagnostic or therapeutic procedures. Often, a catheter tip is placed against the wall of the heart chamber and the three-dimensional coordinates of the catheter tip measured using a localization system. The three-dimensional coordinates become a geometry point. Multiple measurements are taken as the catheter is moved within the heart chamber, resulting in a cloud of geometry points (also referred to as "location data points") that defines the geometry of the heart chamber. Various surface construction algorithms may then be applied to wrap a surface around the cloud of geometry points to obtain a representation of the heart chamber geometry.

While gathering geometry points, it is desirable that the catheter only visit sites within the heart chamber of interest. In practice, however, the catheter will, from time to time, slip into another chamber or structure. For example, in a right atrial study, it is not uncommon for the catheter to slip through the tricuspid valve into the right ventricle. The result of this detour is the acquisition of a large number of erroneous geometry points that must be deleted by the operator in order to input a valid set of geometry points to the surface construction algorithm.

In addition, due to cardiac motion (e.g., the beating of the heart), the catheter may experience oscillations. Depending on how oscillations are accounted for (e.g., by averaging catheter position over one or more heart cycles), it is possible to acquire erroneous geometry points lying outside the true geometry of the beating heart that must be manually deleted to provide a valid set of geometry points to the surface construction algorithm. For example, it the catheter suddenly changes from one generally stable position on the surface of the heart to another generally stable position on the surface of the heart, an averaging or filtering process may create a more or less straight route between the two positions, part of which may lie inside or outside the true boundaries of the heart chamber, while the actual route taken was a curve coincident with the boundaries of the heart chamber.

Further, in order to reduce overhead and time required to perform the surface construction algorithm, it is desirable that the cloud of geometry points include points on the surface of the heart chamber ("surface points") and exclude points not on the surface of the heart chamber ("interior points"). Unfortunately, just as it is not uncommon for the catheter to inadvertently move into an adjoining structure, it is similarly not uncommon for the catheter to occasionally break contact with the surface and fall into the interior of the heart chamber, resulting in the collection of interior points in addition to surface points.

BRIEF SUMMARY OF THE INVENTION

It is desirable, therefore, to be able to distinguish surface points from interior points during the collection of geometry points such that the database of geometry points is limited to surface points.

It is also desirable to be able to distinguish points on the surface of the heart chamber of interest from points elsewhere on the cardiac surface such that only the former are stored during the collection of geometry points.

According to a first aspect of the invention, a method of monitoring contact between a probe and a tissue surface includes the steps of: placing the probe in contact with the tissue surface; moving the probe; periodically measuring a location of the probe; determining a velocity of the probe; and generating a signal indicative of a change in a degree of contact between the probe and the tissue surface based upon the velocity of the moving probe. The step of determining the velocity of the moving probe may include determining a rate of change in the location of the moving probe. Optionally, the step of generating a signal indicative of a change in a degree of contact between the probe and the tissue surface includes: detecting no change in the degree of contact when the velocity of the moving probe falls within a range of acceptable values; detecting a change in the degree of contact when the velocity of the moving probe falls outside of the range of acceptable values; and generating a signal indicative of a change in a degree of contact between the probe and the tissue surface. The range of acceptable values is preferably between about 20 mm/sec and about 120 mm/sec, and more preferably between about 20 mm/sec and about 70 mm/sec.

In another aspect of the present invention, a method of mapping a tissue surface using a probe includes the steps of: placing a distal end of the probe in contact with the tissue surface; moving the probe along at least a portion of the tissue surface; periodically measuring position information for the distal end of the probe to create a measured location data point; storing the measured location data point in a memory to create a plurality of measured location data points; determining a velocity of the distal end of the probe; detecting a loss in contact between the probe and the tissue surface based upon the determined velocity of the distal end of the probe; and generating a 3-D model of the tissue surface using a plurality of measured location data points that are measured while the probe is in contact with the tissue surface. The step of determining a velocity of the distal end of the probe may include determining a velocity of the distal end of the probe for each measured location data point and associating the determined velocity with the measured location data point; the step of detecting a loss in contact may include identifying at least one measured location data point that is not on the tissue surface based on an associated velocity that is in excess of a velocity threshold. Optionally, the step of storing the measured location data points may be suspended for a geometry lockout interval upon detecting a loss in contact. The geometry interval permits the probe to be repositioned on the surface of the tissue, and may be user defined, typically for a period between about 1 second and about 5 seconds. In some embodiments, the geometry lockout interval starts upon detecting that the probe is repositioned on the tissue surface.

In still another aspect of the invention, a method of generating a plurality of location data points defining a model of a tissue surface includes: periodically measuring position information for a probe moving within a subject; determining a velocity of the probe; monitoring the velocity of the probe for an indicator of the probe establishing contact with the tissue surface; deriving, from the measured position information for the probe, a location data point on the tissue surface in contact with the probe; and storing the location data point in a memory. The method may also include monitoring the velocity of the probe for an indicator of the probe losing contact with the tissue surface.

In yet a further aspect of the invention, a method of generating a plurality of location data points defining a model of a tissue surface includes: periodically measuring position information for a probe moving along the tissue surface; determining a velocity of the probe; deriving, from the measured position information for the probe, a location data point on the tissue surface in contact with the probe; storing the location data point in a memory; and monitoring the velocity of the probe for an indicator of the probe losing contact with the tissue surface. Optionally, the method also includes monitoring the velocity of the probe for an indicator of the probe reestablishing contact with the tissue surface.

According to another embodiment of the invention, a system for mapping a tissue surface includes: a probe configured for insertion into a patient for mapping a tissue surface of the patient; a localization system to measure a location data point indicative of the probe's location; a memory coupled to the localization system to store the location data point indicative of the probe's location; a servo mechanism for moving the probe along at least a portion of the tissue surface; a controller coupled to the servo mechanism, the localization system, and the memory to move the probe to a plurality of locations and to record in the memory a plurality of location data points indicative of the plurality of locations; and a contact-sensing processor to analyze the plurality of location data points and to identify a subset of the plurality of location data points on the tissue surface. The system optionally further includes a modeling processor to generate a 3-D model of the tissue surface using the identified subset of the plurality of location data points. The contact-sensing processor may analyze probe velocity to identify the subset of the plurality of location data points. Alternatively, the contact-sensing processor may utilize a low pass filter to process the plurality of location data points to create a first output signal, and analyze at least the first output signal to identify the subset of the plurality of location data points.

In a further aspect of the invention, a method of monitoring contact between a probe and a tissue surface, the probe having a sensor at a distal end thereof, includes: placing the probe in contact with the tissue surface; moving the probe; monitoring a velocity of the moving probe; and generating a signal indicative of a loss of contact with the tissue surface when the monitored velocity of the probe exceeds a velocity threshold.

In another aspect of the invention, a method of monitoring contact between a probe and a tissue surface, the probe having a sensor at a distal end thereof, includes: placing the probe in contact with the tissue surface; moving the probe; using a localization device to monitor movement of the probe; and generating a signal indicative of a loss of contact with the tissue surface when the monitored movement exceeds an expected movement threshold. The signal-generating step may include generating a signal indicative of a loss of contact with the tissue surface when the velocity of the probe exceeds a preset maximum velocity. Alternatively, the signal-generating step may include generating a signal indicative of a loss of contact with the tissue surface when a distance between periodic measurements of probe location information exceeds a preset maximum distance. In still other embodiments, periodically measured location information for the moving probe is stored in a memory, and the stored measurements are filtered at least with a first low pass filter, and optionally with a second low pass filter having a lower cut-off frequency than the first low pass filter, to create first and second output signals. The first and second output signals may be compared, and a signal indicative of a loss of contact may be generated when the first and second output signals diverge by more than an expected amount.

In still another embodiment of the invention, a system for mapping a tissue surface of a patient includes: a probe configured for insertion into the patient to map the tissue surface; a localization system to measure a location data point indicative of the probe's location; a memory coupled to the localization system to store the measured location data point; a mechanism adapted to allow an operator to move the probe along at least a portion of the tissue surface; and a contact sensing processor to analyze the plurality of location data points and to identify a subset of the plurality of location data points, wherein the subset includes location data points on the tissue surface and excludes location data points interior to the tissue surface. The mechanism may be a servo mechanism, which may be coupled to a suitable controller, or, alternatively, the mechanism may be a handle for manual operation.

An advantage of the invention is that it reduces the processor time and overhead necessary to generate a 3-D model of a tissue surface.

Another advantage of the invention is that a user of the system need not manually delete invalid or undesired geometry points prior to generating a 3-D model of a tissue surface.

Yet another advantage of the invention is that it reduces the likelihood of generating geometry points that lie outside of the boundaries of a beating heart.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 5b plots the absolute value of the difference between the first and second filtered output signals illustrated in FIG. 5a.

DETAILED DESCRIPTION OF THE INVENTION

Figure 1:
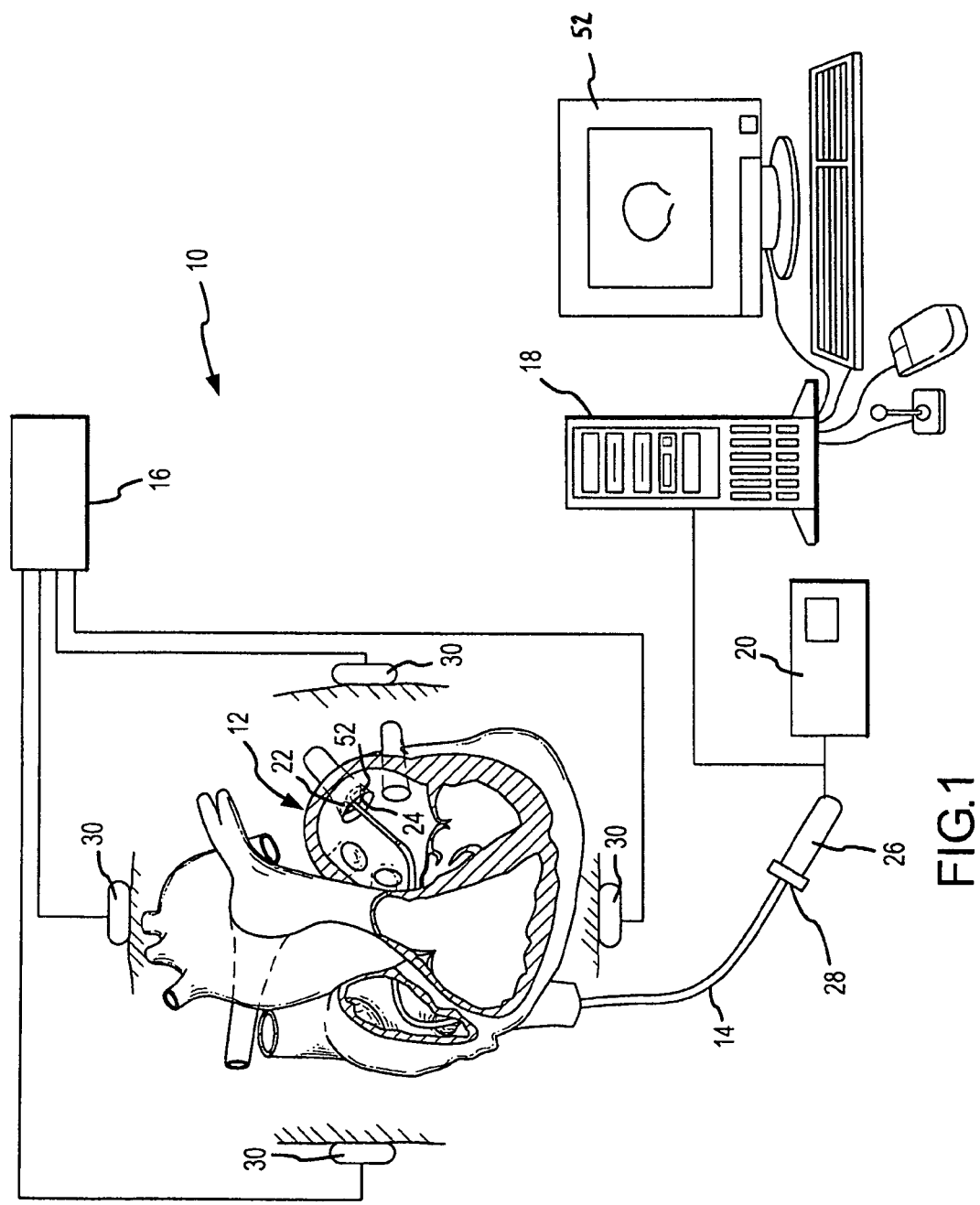
FIG. 1 is a schematic illustration of a tissue mapping system.

Referring now to the figures, and in particular to FIG. 1, there is shown a schematic illustration of a system 10 for mapping a tissue surface. Mapping system 10 filters surface points from interior points while acquiring location data points and generates a surface model utilizing the surface points. For purposes of this disclosure, the system 10 will be described in connection with mapping and modeling of a tissue surface within a patient's heart 12, though one of ordinary skill in the art will appreciate that the system 10 and its applications are not so limited. The system 10 generally includes a probe 14, a localization system 16 (sometimes also referred to as a "navigation system," "mapping system," or "positional feedback system"), a memory, such as a hard drive or random access memory (RAM) module, which may be part of a computer system 18, a servo mechanism 20, a controller, and a contact-sensing processor. The controller and the contact-sensing processor may also be part of computer system 18.

Probe 14 is configured for insertion into the patient, and particularly into the patient's heart 12, for mapping a cardiac tissue surface. Probe 14 is preferably an intra-cardiac catheter, though other devices are contemplated. Probe 14 carries at least one sensor, such as electrode 22 thereon, preferably at a distal end 24 of probe 14. Probe 14 may be robotically moved along at least a portion of the tissue surface of heart 12 via servo mechanism 20. Alternatively, a user, such as a cardiologist, may move probe 14 by actuating a control handle 26 at a proximal end 28 of probe 14.

Localization system 16 measures a location data point indicative of the location of probe 14 within heart 12. Localization system 16 may include a plurality of paired electrodes 30 defining measurement axes for locating probe 14 within heart 12 by utilizing the electrical potentials measured by electrode 22. Preferably, localization system 16 is the EnSite NavX™ navigation and visualization system of St. Jude Medical, Inc., though other localization systems (including, e.g., the CARTO navigation system from Biosense Webster, Inc.) may be utilized without departing from the spirit and scope of the present invention. For purposes of this description, localization system 16 provides location data points for probe 14 within heart 12 relative to a three-dimensional Cartesian coordinate system including an x-axis, a y-axis, and a z-axis. Thus, the $i^{th}$ position for probe 14 can be expressed as a coordinate point $(x_i, y_i, z_i)$. It should be understood, however, that alternative systems of measuring and/or expressing position information for probe 14, such as spherical coordinates, are contemplated. The memory is coupled to localization system 16 to store the location data point indicative of the location of probe 14.

The controller is coupled to servo mechanism 20, localization system 16, and the memory to move probe 14 to a plurality of locations within heart 12, and to record in the memory the measured location data points indicative of the plurality of locations, thereby generating a plurality of location data points. As one of ordinary skill in the art will appreciate, the plurality of location data points defines the volume occupied by the portion of heart 12 being mapped.

The contact-sensing processor is programmed to analyze the plurality of location data points and to identify a subset of the plurality of location data points that are on the surface of heart 12. That is, the contact-sensing processor identifies those points within the plurality of location data points that are surface points. Preferably, the contact-sensing processor identifies the surface points by analyzing a velocity of probe 14 as it moves. That is, the contact-sensing processor analyzes a rate of change in the location of probe 14 with respect to time.

Mapping system 10 may also include a modeling processor, which, for the purposes of this disclosure, will be described as integrated into computer system 18. It should be understood that the modeling processor may also be independent from computer system 18. The modeling processor is programmed to generate a 3-D model of the tissue surface of heart 12 using at least the surface points. The modeling processor preferably applies a surface construction algorithm, such as a shrink wrap algorithm, a marching cubes algorithm, a marching tetrahedrons algorithm, or another suitable algorithm, in order to wrap a surface about the surface points. Since the contact-sensing processor identifies the surface points, and excludes interior points, the time and overhead required by the modeling processor to generate the 3-D model of the tissue surface of heart 12 are advantageously reduced. Further, since the contact-sensing processor distinguishes surface points from interior points, there is a greatly reduced need for an operator to cull out invalid points.

For purposes of this disclosure, the controller, the contact-sensing processor, and the modeling processor are described and illustrated as integrated within computer system 18. It is contemplated, however, that multiple computer systems may be used to practice the present invention. Further, the functions of the controller, the contact-sensing processor, and the modeling processor may be executed by separate processors within computer system 18 without departing from the scope of the present invention.

Figure 2:
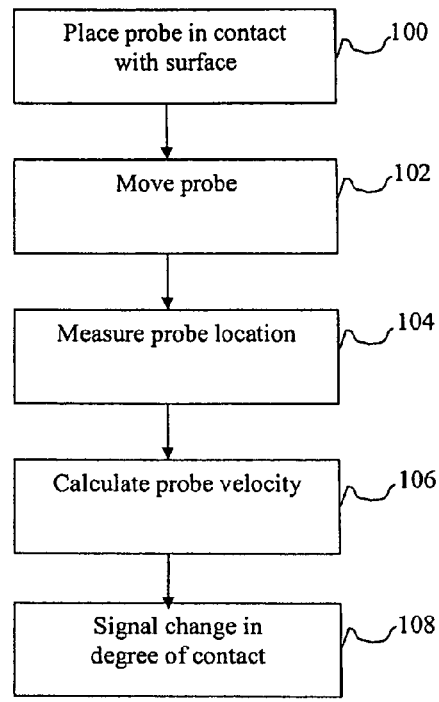
FIG. 2 is a flowchart of a method of monitoring contact between a probe and a tissue surface according to an embodiment of the present invention.

A method of monitoring contact between probe 14 and the tissue surface will be described with reference to FIG. 2. In block 100, probe 14 is placed in contact with the tissue surface. In block 102, probe 14 is moved, and the location of probe 14 is periodically measured in block 104. The velocity of probe 14 is determined in block 106. In block 108, a signal indicative of a change in a degree of contact between probe 14 and the tissue surface is generated based upon the velocity of probe 14. The term "degree of contact" refers to the relationship between probe 14 and the tissue surface; that is, it encompasses not only whether or not probe 14 and the tissue surface are in contact, but also how hard probe 14 is pressing into the tissue surface.

In keeping with the Cartesian coordinate system described above, a first measured location of probe 14 measured at a first time may be expressed as $(x_1, y_1, z_1)$, and a second measured location of probe 14 measured at a second time may be expressed as $(x_2, y_2, z_2)$. Thus, the distance d between the first and second measured locations of probe 14 is given by the equation $$d=\sqrt{(x_2-x_1)^2+(y_2-y_1)^2+(z_2-z_1)^2}.$$

Preferably, position information for probe 14 is periodically measured at a substantially constant sampling rate $F_s$. Thus, the velocity v of probe 14 may be calculated as $v=d \cdot F_s$. It is also contemplated, however, that position information for probe 14 may be measured episodically (that is, with a variable interval between successive measurements). In this case, the velocity v of probe 14 may be calculated as $d/\Delta t$, where $\Delta t$ is the time interval between the episodic measurements. For both periodic and episodic measurements, however, the velocity v of probe 14 is a function of the distance d probe 14 travels between location data point measurements. That is, as should be commonly understood, and as described above, the velocity of probe 14 is a rate of change in the location of probe 14 with respect to time.

For a given $F_s$, and assuming no change in contact between probe 14 and the tissue surface, there exist expected values for both d and v between measurements of the position of probe 14. These expected values may be expressed as a range of acceptable values between a lower limit LL and an upper limit UL. Alternatively, the expected values may be expressed as a distance threshold $d_t$ or velocity threshold $v_t$, which, when crossed, indicates a change in the degree of contact between the probe 14 and the tissue surface. The velocity threshold $v_t$ is preferably between about 20 mm/sec and about 120 mm/sec, and more preferably is about 70 mm/sec. It is also contemplated that the range of acceptable values, distance threshold, and velocity threshold may be user-adjustable.

Figures 3A, 3B:
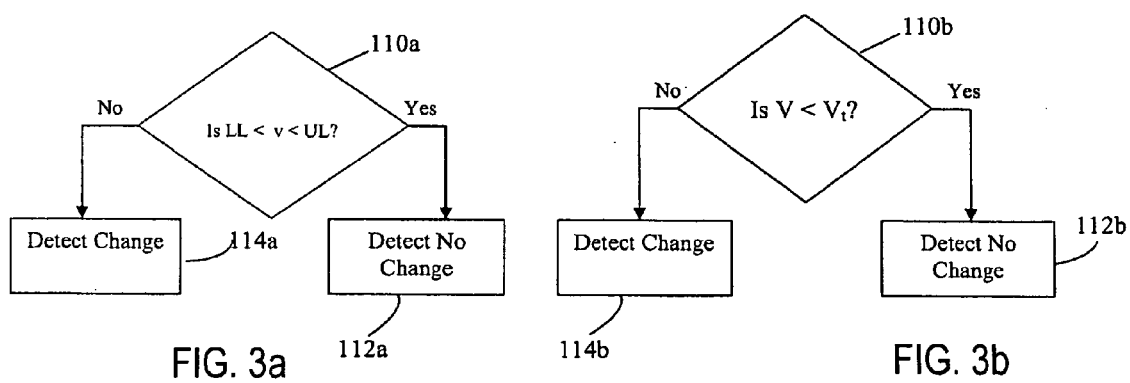
FIGS. 3a and 3b are exemplary decision blocks utilized by the method of FIG. 2 to detect a change in a degree of contact between the probe and the tissue surface.

Accordingly, as seen in FIG. 3a, decision block 110a determines whether the velocity v of probe 14 falls within a range of acceptable values between LL and UL. If LL<v<UL, then no change is detected (block 112a). If, however, v does not fall between LL and UL, then a change is detected (block 114a). Similarly, as seen in FIG. 3b, if v<$v_t$ (block 110b), then no change is detected (block 112b). If, however, v>$v_t$, then a change is detected (block 114b).

Therefore, by monitoring the velocity of probe 14, it is possible to identify, and generate a signal indicative of, a loss of contact between probe 14 and the tissue surface when the velocity exceeds a velocity threshold (i.e., a preset maximum velocity). More generally, by monitoring movement of probe 14 via localization device 16, it is possible to identify, and generate a signal indicative of, a loss of contact between probe 14 and the tissue surface when the monitored movement exceeds an expected movement threshold. Thus, it is also contemplated to generate the signal indicative of the loss of contact between probe 14 and the tissue surface when the distance d between periodic measurements of the location of probe 14 exceeds a distance threshold $d_t$ (i.e., a preset maximum distance).

Figure 4A:
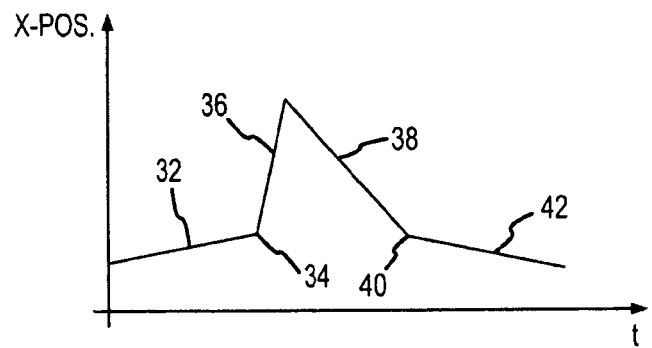
FIG. 4a is a representative graph of probe x-axis position as a function of time.
Figure 4B:
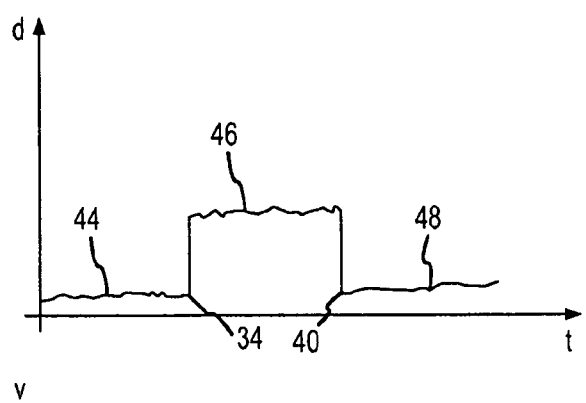
FIG. 4b is a representative graph of the distance profile of a probe as a function of time.
Figure 4C:
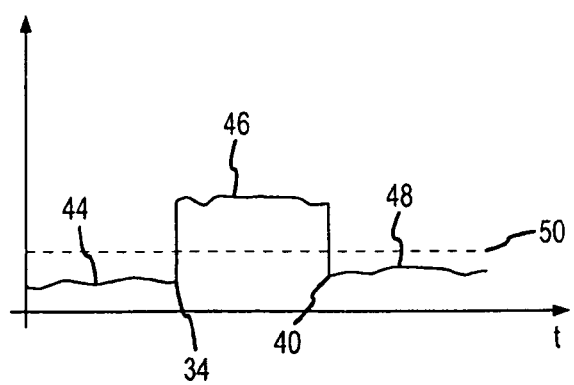
FIG. 4c is a representative graph of the velocity profile of a probe as a function of time.

FIGS. 4a-4c illustrate exemplary position, distance, and velocity profiles of probe 14 over time and along a single axis. The x-axis position of probe 14 over time is shown in FIG. 4a. For the sake of convenience, probe 14 is shown having only positive x values. At time t=0, probe 14 is in contact with the tissue surface. Within region 32, probe 14 is moving along the tissue surface, and thus experiences only very small changes in position between measurements due to friction between probe 14 and the tissue surface. The slope of region 32 is therefore relatively shallow. At point 34, however, probe 14 loses contact with the tissue surface, and exhibits a large change in position between measurements. In regions 36 and 38, probe 14 is moving while not in contact with the tissue surface; region 36 may represent probe 14 initially breaking contact with the tissue surface, while region 38 may represent the physician's efforts to reestablish contact between probe 14 and the tissue surface. Since there is considerably less resistance to slow probe 14 when it is moving in the interior of heart 12, the slope of regions 36 and 38 is steeper than the slope in region 32. At point 40, probe 14 reestablishes contact with the tissue surface and resumes moving therealong in region 42.

FIG. 4b illustrates the relationship between distance d moved by probe 14 between measurements and time, while FIG. 4c illustrates the rate of change in d over time (that is, the velocity of probe 14). Regions 44 in FIGS. 4b and 4c correspond to region 32 of FIG. 4a, and thus show relatively small distances and low velocities. Regions 46 in FIGS. 4b and 4c correspond to regions 36 and 38 of FIG. 4a, and thus show larger distances and higher velocities. Finally, regions 48 in FIGS. 4b and 4c correspond to region 42 of FIG. 4a, and thus once again show relatively small distances and low velocities. FIG. 4c further illustrates line 50, v=$v_t$, demonstrating the maximum velocity above which a change in degree of contact is detected.

According to another embodiment of a method for monitoring contact between probe 14 and the tissue surface, the periodically measured location information of probe 14 is stored within the memory. The stored periodic measurements are then filtered with first and second low pass filters to generate respective first and second output signals. The first low pass filter has a cut-off frequency F1, while the second low pass filter has a cut-off frequency F2, with F2 being less than F1.

Since F1 and F2 differ, there may be divergence between the first and second output signals. For relatively small movements of probe 14 along the tissue surface, the divergence between the first and second output signals will be relatively small. For larger movements, such as would be associated with probe 14 breaking contact with the tissue surface, the divergence between the first and second output signals will be larger. Thus, by comparing the first and second output signals, a signal indicative of a loss of contact between probe 14 and the tissue surface may be generated when the first and second output signals diverge by more than an expected amount. As one of skill in the art will appreciate, the expected amount will typically be associated with probe 14 maintaining contact with the tissue surface, and it is contemplated that the expected amount may be user defined.

Figure 5A:
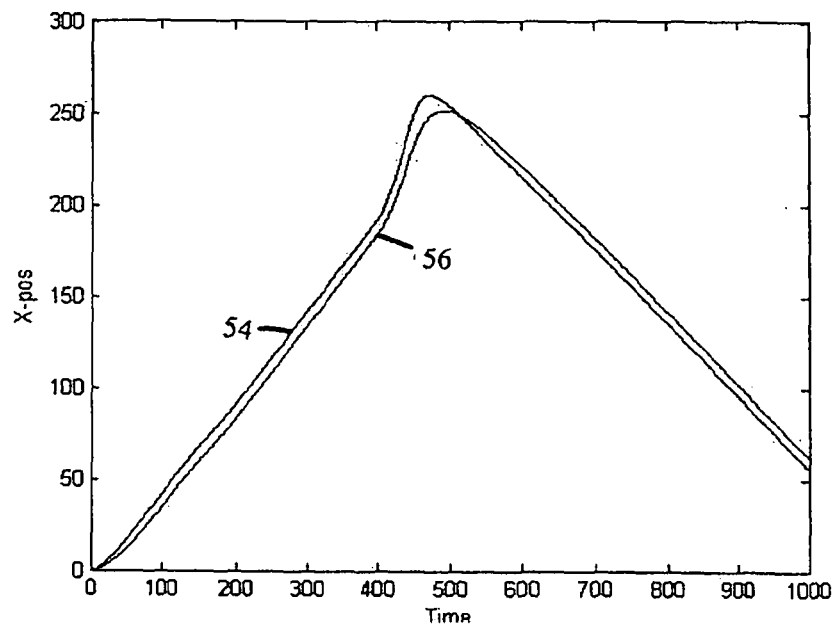
FIG. 5a is a representative graph of first and second filtered output signals of probe x-axis position as a function of time.
Figure 5B:
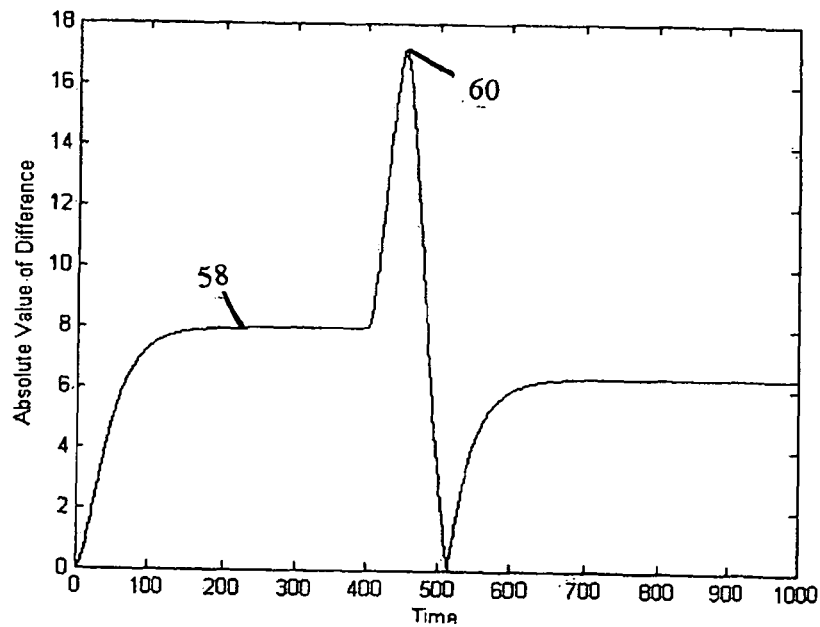

FIG. 5a graphically illustrates representative first output signal 54 and second output signal 56 of the x-position of probe 14 as a function of time. As seen on the left-hand side of the plot, first and second output signals 54, 56 exhibit a relatively small, generally constant divergence while probe 14 is in contact with the tissue surface (region 58 in FIG. 5b). When probe 14 breaks contact with the tissue surface, however, a spike 60 (FIG. 5b) in the divergence between first and second output signals 54, 56 is observed.

Similarly, in another embodiment of a method of monitoring contact between probe 14 and the tissue surface, the periodically measured location information of probe 14 is stored within the memory, which generates a first, unfiltered output signal including a plurality of location information measurements. The stored periodic measurements may then be subjected to low pass filtering to create a second output signal. As described above, by comparing the first and second output signals, a signal indicative of a loss of contact between probe 14 and the tissue surface may be generated when the first and second output signals diverge by more than an expected amount.

Figure 6:
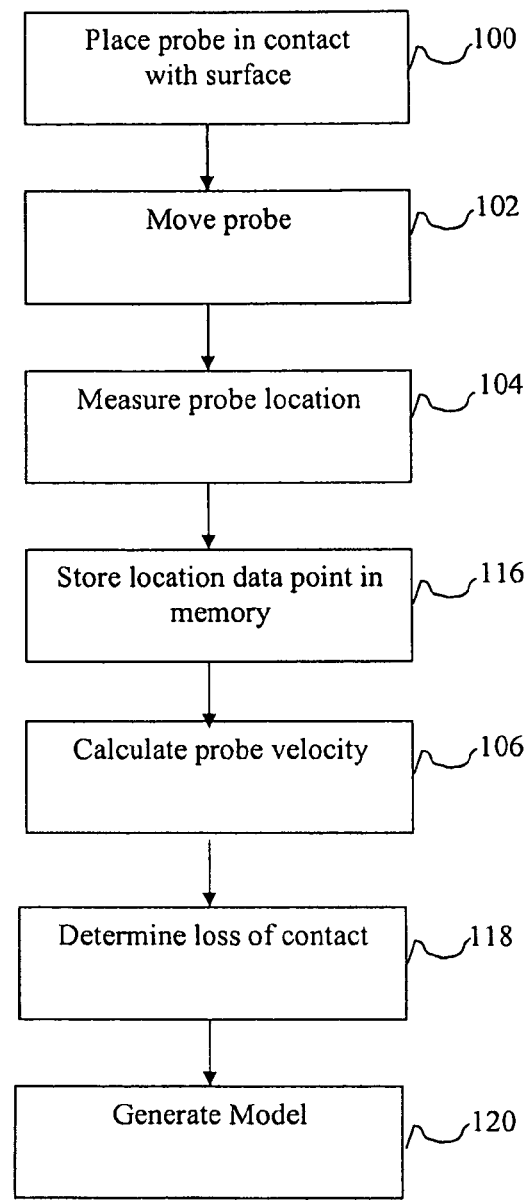
FIG. 6 is a flowchart of a method of creating a model of a tissue surface according to an embodiment of the present invention.

The methods of monitoring contact between probe 14 and the tissue surface described herein may advantageously be employed in mapping the tissue surface. Specifically, the contact sensing methods disclosed herein may be used to distinguish surface points from interior points. One embodiment of a mapping method is illustrated in the flowchart of FIG. 6. Steps 100, 102, and 104 are as described above in connection with FIG. 2. Thus, distal end 24 of probe 14 is placed in contact with the tissue surface and moved along at least a portion thereof while periodically measuring position information of distal end 24 to create a measured location data point. In step 116, the measured location data point is stored in the memory, whereby a plurality of location data points is created. The plurality of location data points defines the geometry of heart 12.

The velocity of distal end 24 of probe 14 is determined in step 106. In step 118, a loss in contact between probe 14 and the tissue surface is detected based upon the velocity determined in step 106. Finally, in step 120, a 3-D model of the tissue surface of heart 12 is generated using a plurality of measured location points that are measured while probe 14 is in contact with the tissue surface (i.e., the subset of the plurality of measured location points that are surface points). A display 52, which may be coupled to computer system 18, may be used to graphically present the model of the tissue surface.

As described above, the contact-sensing processor identifies the surface points, preferably based on the velocity of distal end 24 of probe 14. Accordingly, in some embodiments of the invention, a velocity of distal end 24 of probe 14 is determined for, and associated with, each measured location data point. By identifying those measured location data points with an associated velocity in excess of a velocity threshold, the contact-sensing processor, as opposed to the modeling processor or an operator, may distinguish surface points from interior points.

Preferably, the measured position information for distal end 24 of probe 14 is not stored in the memory when distal end 24 of probe 14 is not in contact with the tissue surface, such that the plurality of measured location data points only includes surface points and excludes interior points. Thus, in some embodiments of the invention, any measured location data point associated with a velocity outside of acceptable limits or in excess of a velocity threshold is simply excluded from the memory (that is, not stored), while other points are included in the memory (that is, stored). If an initially excluded location data point is, in fact, legitimate, the user simply needs to retain probe 14 in the same position until the next measurement. Since probe 14 is not moved, or is moved only very slightly, the velocity associated with the next measured location data point will be diminishingly small, and the measured location data point will be stored in the memory.

While such a simple exclusion/inclusion rule is contemplated, the contact-sensing processor preferably employs a selective storage subroutine to more effectively coordinate creation of the plurality of measured location data points with contact between probe 14 and the tissue surface of heart 12. In some embodiments of the invention, upon detecting a loss in contact between probe 14 and the tissue surface, step 116 of storing the measured location data points is suspended for a preset geometry lockout interval. The geometry lockout interval provides the user with time in which to reposition probe 14 on the tissue surface. The geometry interval may be user defined, and is preferably between about 1 second and about 5 seconds, and more preferably between about 2 seconds and about 3 seconds.

Preferably, the geometry lockout interval is "retriggerable," meaning that it restarts upon measuring a location data point having a velocity in excess of the velocity threshold. Thus, with reference to FIG. 4c, the geometry lockout interval is constantly resetting in region 46 such that it cannot elapse until after the velocity drops below the velocity threshold at point 40.

Similar functionality may be provided by starting the geometry lockout interval upon detecting that probe 14 has reestablished contact with the tissue surface. Thus, with reference to FIG. 4c, step 116 would be suspended at point 34 when probe 14 breaks contact with the tissue surface (i.e., when $v > v_t$), and the geometry lockout interval would start at point 40 when probe 14 reestablishes contact with the tissue surface (i.e., when $v < v_t$).

In both instances, for as long as the velocity of probe 14 exceeds the velocity threshold, step 116 of storing the measured location data point remains suspended. Once the geometry interval has elapsed, step 116 of storing the measured location data point may resume.

As an alternative to a fixed geometry interval, it is contemplated that step 116 may be suspended when a loss in contact is detected, and resumed when a reestablishment of contact is detected. Thus, with reference to FIG. 4c, step 116 is suspended at point 34 when $v > v_t$, and is resumed at point 40 when $v < v_t$. That is, geometry points are not collected while probe 14 is moving faster than the velocity threshold, and collection resumes when probe 14 has once again slowed down below the velocity threshold. This alternative is also well suited to the embodiment of the present invention that senses contact based on signal divergence.

The embodiments and aspects of the invention described above assume that probe 14 starts in contact with the tissue surface and first detects a loss of contact between probe 14 and the tissue surface. Since the methods disclosed herein detect changes in the degree of contact between probe 14 and the tissue surface, however, it may also be utilized to detect establishment of contact between probe 14 and the tissue surface as probe 14 is introduced into the patient. Thus, position information for probe 14 may be periodically measured as probe 14 moves within the subject, and the velocity of probe 14 determined therefrom. The contact-sensing processor may monitor the velocity of probe 14 for an indicator of probe 14 establishing contact with the tissue surface. Position information for a point on the tissue surface in contact with probe 14 may be derived from the measured position information for probe 14 and stored in the memory. Subsequently, the velocity of probe 14 may be monitored for an indicator of probe 14 losing contact with the tissue surface.

Though electrode 22 is preferably located at distal end 24 of probe 14, such that the position of electrode 22 generally corresponds to a point on the surface of heart 12, one of ordinary skill in the art will appreciate that position information for points on the surface of heart 12 in contact with probe 14 may equally well be derived from a known relationship between distal end 24 and another point on probe 14 where a position sensor or electrode is located. Thus, for example, if the position sensor or electrode is located at position 52, rather than at distal end 24, the measured position information of probe 14 will not correspond to location information for a point on the surface of heart 12, but such location information can be derived therefrom.

Although several aspects and embodiments of this invention have been described above with a certain degree of particularity, those skilled in the art could make numerous alterations to the disclosed embodiments without departing from the spirit or scope of this invention. For example, though the system and method has been described in connection with a medical procedure, and in particular the generation of a surface model of a heart chamber, one of ordinary skill in the art will appreciate that the system and method could be used to model any body cavity, internal organ, or other surface of interest. In addition, though the system and method are described in connection with a single electrode, multiple electrodes could be employed without departing from the spirit and scope of the present invention. In embodiments utilizing multiple electrodes, preferably only data from "active" electrodes (i.e., those from which position information is being measured) will initiate the geometry lockout interval.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of monitoring a degree of contact between a probe and a tissue surface within a patient's body, comprising:
    moving the probe within the patient's body;
    measuring a location of the probe a plurality of times as it moves; and
    generating a signal indicative of a change in a degree of contact between the probe and the tissue surface based upon a distance moved by the probe over time,
    wherein the step of generating a signal indicative of a change in a degree of contact between the probe and the tissue surface based upon a distance moved by the probe over time comprises:
        converting the plurality of measured locations of the probe into a first output signal;
        filtering the plurality of measured locations of the probe using a low pass filter to create a second output signal;
        comparing the first output signal with the second output signal; and
        generating a signal indicative of a change in a degree of contact between the probe and the tissue surface if the first output signal and the second output signal diverge by more than an expected amount.

2. The method according to claim 1, wherein the step of generating a signal indicative of a change in a degree of contact between the probe and the tissue surface based upon a distance moved by the probe over time comprises:
    determining a rate of change of the location of the probe with respect to time; and
    generating a signal indicative of a change in a degree of contact between the probe and the tissue surface based upon the rate of change of the location of the probe with respect to time.

3. The method according to claim 2, wherein the step of generating a signal indicative of a change in a degree of contact between the probe and the tissue surface based upon the rate of change of the location of the probe with respect to time comprises generating a signal indicative of an increase in the degree of contact between the probe and the tissue surface when the rate of change of the location of the probe with respect to time is less than an expected rate of change.

4. The method according to claim 2, wherein the step of generating a signal indicative of a change in a degree of contact between the probe and the tissue surface based upon the rate of change of the location of the probe with respect to time comprises generating a signal indicative of a decrease in the degree of contact between the probe and the tissue surface when the rate of change of the location of the probe with respect to time is greater than an expected rate of change.

5. The method according to claim 2, wherein the step of determining a rate of change of the location of the probe with respect to time comprises measuring a velocity of the probe.

6. The method according to claim 2, wherein the step of determining a rate of change of the location of the probe with respect to time comprises computing a velocity of the probe from successive measured locations of the probe.

7. The method according to claim 1, wherein the step of generating a signal indicative of a change in a degree of contact between the probe and the tissue surface based upon a distance moved by the probe over time comprises generating a signal indicative of an increase in the degree of contact between the probe and the tissue surface when the distance moved by the probe over time is less than an expected distance.

8. The method according to claim 1, wherein the step of generating a signal indicative of a change in a degree of contact between the probe and the tissue surface based upon a distance moved by the probe over time comprises generating a signal indicative of a decrease in the degree of contact between the probe and the tissue surface when the distance moved by the probe over time is greater than an expected distance.

9. A system for mapping a tissue surface of a patient, comprising:
    a probe configured for insertion into the patient to map the tissue surface;
    a localization system to measure a location data point indicative of the probe's location;
    a memory coupled to the localization system to store the measured location data point; and
    a contact-sensing processor configured to analyze the location data point and determine whether the location data point is on the tissue surface or interior to the tissue surface based on a rate of change in position information of the probe with respect to time when the location data point is measured,
    wherein the contact-sensing processor determines whether the location data point is on the tissue surface or interior to the tissue surface by:
        converting a plurality of measured location data points into a first output signal;
        filtering the plurality of measured location data points using a low pass filter to create a second output signal;
        comparing the first output signal with the second output signal; and
        determining whether the location data point is on the tissue surface or interior to the tissue surface based upon a divergence between the first output signal and the second output signal.

10. The system according to claim 9, wherein the measured location data point is only stored in the memory if the contact-sensing processor determines that the location data point is on the tissue surface.

11. A system for mapping a tissue surface of a patient, comprising:
    a probe configured for insertion into the patient;
    a localization system to measure a location data point indicative of the probe's location within the patient;
    means for discriminating between location data points on the tissue surface of the patient and points not on the tissue surface of the patient based on a distance moved by the probe over time; and
    means for rendering a three dimensional model of the tissue surface of the patient from a plurality of location data points on the tissue surface of the patient,
    wherein the means for discriminating between location data points on the tissue surface of the patient and points not on the tissue surface of the patient is configured to:
        convert a plurality of measured location data points into a first output signal;
        filter the plurality of measured location data points using a low pass filter to create a second output signal;
        compare the first output signal with the second output signal; and discriminate between location data points on the tissue surface of the patient and points not on the tissue surface of the patient based upon a divergence between the first output signal and the second output signal.

12. A method of monitoring a degree of contact between a probe and a tissue surface within a patient's body, comprising:

moving the probe within the patient's body;

measuring a location of the probe a plurality of times as it moves; and generating a signal indicative of a change in a degree of contact between the probe and the tissue surface based upon a distance moved by the probe over time, wherein the step of generating a signal indicative of a change in a degree of contact between the probe and the tissue surface based upon a distance moved by the probe over time comprises:

filtering the plurality of measured locations of the probe using a first low pass filter to create a first output signal, the first low pass filter having a cut-off frequency of F1;

filtering the plurality of measured locations of the probe using a second low pass filter to create a second output signal, the second low pass filter having a cut-off frequency of F2, wherein F2 is less than F1;

comparing the first output signal with the second output signal; and generating a signal indicative of a change in a degree of contact between the probe and the tissue surface if the first output signal and the second output signal diverge by more than an expected amount.

* * * * *